United States Patent
Zhu et al.

(10) Patent No.: US 11,614,408 B2
(45) Date of Patent: Mar. 28, 2023

(54) METHOD FOR IMPROVING IDENTIFICATION ACCURACY OF MIXTURE COMPONENTS BY USING KNOWN MIXTURE RAMAN SPECTRUM

(71) Applicant: JIANGNAN UNIVERSITY, Wuxi (CN)

(72) Inventors: Qibing Zhu, Wuxi (CN); Mingqiang Ji, Wuxi (CN); Min Huang, Wuxi (CN); Ya Guo, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 182 days.

(21) Appl. No.: 17/344,111

(22) Filed: Jun. 10, 2021

(65) Prior Publication Data
US 2021/0364441 A1 Nov. 25, 2021

Related U.S. Application Data

(63) Continuation of application No. PCT/CN2020/135144, filed on Dec. 10, 2020.

(30) Foreign Application Priority Data

May 19, 2020 (CN) .......................... 202010424783.1

(51) Int. Cl.
G01J 3/44 (2006.01)
G01N 21/65 (2006.01)
(52) U.S. Cl.
CPC ................ G01N 21/65 (2013.01); G01J 3/44 (2013.01)
(58) Field of Classification Search
CPC ... G01N 21/65; G01N 2201/1293; G01J 3/44; G16C 20/20; G06F 2218/10; A61B 5/0075
See application file for complete search history.

(56) References Cited

U.S. PATENT DOCUMENTS

| 8,013,991 B2 * | 9/2011 | Maier | ..................... | G06V 20/69 |
| | | | | 356/73 |
| 2012/0065899 A1 * | 3/2012 | Sato | ....................... | G01N 21/65 |
| | | | | 702/23 |

FOREIGN PATENT DOCUMENTS

| CN | 104458693 A | 3/2015 |
| CN | 108169213 A | 6/2018 |

(Continued)

OTHER PUBLICATIONS

Ji et al., "Method for improving identification accuracy of components in mixtures using Raman spectra of known mixtures" Chinese Journal of Lasers, vol. 47, No. 11, Nov. 2020, pp. 1-13 (Jul. 15, 2020).

(Continued)

*Primary Examiner* — Abdullahi Nur
(74) *Attorney, Agent, or Firm* — SZDC Law P.C.

(57) ABSTRACT

A method for improving an identification accuracy of mixture components by using a known mixture Raman spectrum is disclosed. After calculating a first similarity between a to-be-tested Raman spectrum characteristic vector group and a pure substance Raman spectrum characteristic vector group of an nth kind of pure substance in a Raman spectrum standard library, the method uses a known mixture library to calculate to obtain a second similarity between a to-be-identified substance Raman spectrum characteristic vector group and a spectral peak characteristic vector group with offset information corresponding to a pure substance in a known mixture, and determines a similarity between a to-be-tested mixture and the nth kind of pure substance according to the first similarity and all second similarities to thus obtain a component identification result. The present application uses the known mixture library to assist the Raman spectrum standard library in searching.

6 Claims, 2 Drawing Sheets

(56) References Cited

FOREIGN PATENT DOCUMENTS

| | | |
|---|---|---|
| CN | 108398416 A | 8/2018 |
| CN | 108780047 A | 11/2018 |
| CN | 109557071 A | 4/2019 |
| CN | 109738413 A | 5/2019 |
| CN | 110243806 A | 9/2019 |
| EP | 2162729 A1 | 3/2010 |
| JP | 2014153098 A | 8/2014 |

OTHER PUBLICATIONS

Liu et al. "Indentification of components in mixtures based on Raman spectroscopy" Laser & Optoelectronics Progress, vol. 56, No. 8, Apr. 2019, pp. 1-7 (Apr. 30, 2019).

Liu et al. "Ramn spectrum library matching method based on integrated features" Chinese Journal of Lasers, vol. 46, No. 1, Jan. 2019, pp. 1-8 (Jan. 31, 2019).

* cited by examiner

METHOD FOR IMPROVING IDENTIFICATION ACCURACY OF MIXTURE COMPONENTS BY USING KNOWN MIXTURE RAMAN SPECTRUM

This application is a Continuation Application of PCT/CN2020/135144, filed on Dec. 10, 2020, which claims priority to Chinese Patent Application No. 202010424783.1, filed on May 19, 2020, which is incorporated by reference for all purposes as if fully set forth herein.

TECHNICAL FIELD

The present invention relates to the technical field of Raman spectra, and in particular, to a method for improving an identification accuracy of mixture components by using a known mixture Raman spectrum.

BACKGROUND

Raman spectroscopy is a spectral analysis technology, which is widely applied in the field of analysis of sample composition and content. It analyzes scattered spectra with different incident light frequencies to obtain molecular vibration and rotation information, and is applied to analysis of material composition (qualitative analysis) and concentration (quantitative analysis). The spectral peaks of the Raman spectrum of a tested substance correspond to some specific substance molecules. Different substances have different chemical bonds or functional groups, resulting in different spectral peaks on the Raman spectrum. Therefore, the Raman spectrum is also called "fingerprint" spectrum. Due to its advantages of quickness, simplicity, non-invasion and no need to preprocess samples, the Raman spectrum is widely used in the fields of archaeology, biology, substance identification, etc.

The identification of mixture components is of great significance in the analysis of mixtures. In the field of qualitative identification of mixtures based on Raman spectrum, identification methods usually include a spectral peak contrast method, a projection method, a neural network method, etc. Although these methods have gained certain achievements, they usually cannot meet people's requirements for mixture identification due to the disadvantages of relying on human subjective judgment, wasting time and labor, requiring a large number of training samples, etc.

At present, a commonly used search algorithm is based on a Raman spectrum database of pure substances. The basic principle is to construct a Raman spectrum database of known pure substances, compare the spectrum of a to-be-identified substance with the spectra in the Raman spectrum database one by one, calculate the similarity therebetween, and finally determine components of the to-be-identified mixture according to the degree of the similarity. In specific applications, due to a repeatability error of a measuring instrument itself and the related interferences of respective components in the to-be-identified mixture, both the spectral peaks of the Raman spectra of respective components in the collected mixture and the pure substance spectral peaks in the Raman spectrum database have an offset phenomenon to a certain extent, which affects the identification accuracy of the mixture components. To reduce the offset phenomenon of the spectral peaks of the Raman spectra, it is usually necessary for the measuring instrument to control its measurement environment and perform spectral calibration during use. However, for devices such as handheld Raman spectrometers for rapid detection applications, the measurement environment is often difficult to control, and the spectrum correction is difficult, which leads to relatively serious misidentification problems in case of a relatively large Raman spectrum database, and thus the accuracy of qualitative identification is hard to guarantee.

SUMMARY

In view of the above problems and technical requirements, the inventor of the present invention proposes a method for improving an identification accuracy of mixture components by using a known mixture Raman spectrum, and the method includes the following steps:

establishing a Raman spectrum standard library and a known mixture library, wherein the Raman spectrum standard library includes pure substance Raman spectrum characteristic vector groups of N kinds of pure substances; the known mixture library includes known mixture Raman spectrum characteristic vector groups of M kinds of known mixtures; and each kind of the known mixtures is formed by mixing K kinds of pure substances;

acquiring a to-be-tested Raman spectrum characteristic vector group of a to-be-tested mixture;

calculating a first similarity between the to-be-tested Raman spectrum characteristic vector group and a pure substance Raman spectrum characteristic vector group of an nth kind of pure substance in the Raman spectrum standard library, and detecting whether a reference known mixture exists in the known mixture library, wherein the reference known mixture is a known mixture containing the nth kind of pure substance from among the M kinds of known mixtures; n is a parameter, and a starting value of n is 1;

if no reference known mixture exists in the known mixture library, determining that a similarity between the to-be-tested mixture and the nth kind of pure substance is the first similarity;

if Q kinds of reference known mixtures exist in the known mixture library, extracting a spectral peak characteristic vector group with offset information corresponding to the nth kind of pure substance in the known mixture Raman spectrum characteristic vector group of each kind of reference known mixture, and calculating a second similarity between the spectral peak characteristic vector group with the offset information and the to-be-tested Raman spectrum characteristic vector group; and determining that the similarity between the to-be-tested mixture and the nth kind of pure substance is a maximum value from the first similarity and Q second similarities;

after determining that the similarity between the to-be-tested mixture and the nth kind of pure substance is obtained, setting n=n+1, and re-executing steps of calculating the first similarity between the to-be-tested Raman spectrum characteristic vector group and the pure substance Raman spectrum characteristic vector group of the nth kind of pure substance in the Raman spectrum standard library and detecting whether a reference known mixture exists in the known mixture library, till N similarities between the to-be-tested mixture and the N kinds of pure substances are obtained in case of n=N; and selecting P kinds of pure substances with the highest similarity as a component identification result of the to-be-tested mixture.

Beneficial technical effects of the present invention are as follows:

The present application uses the known mixture library to assist the Raman spectrum standard library in searching. Compared with a strategy that only uses a pure substance library for searching, the application of the known mixtures of the present application effectively compensates for the interference caused by the offset phenomenon and can effectively help to improve the identification accuracy of a to-be-identified substance.

DETAILED DESCRIPTION

Specific implementations of the present invention will be further described below with reference to the accompanying drawings.

Figure 1:
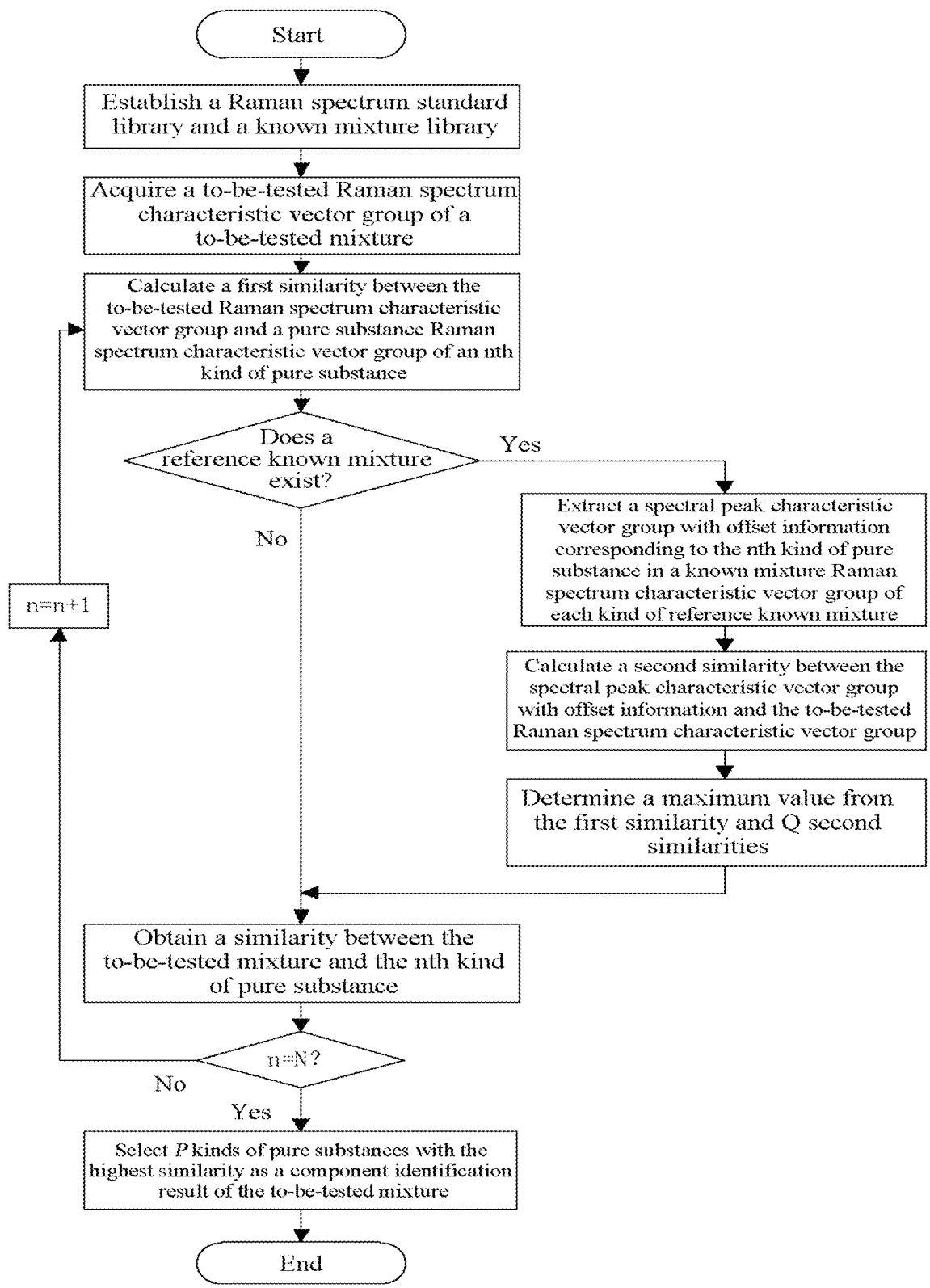
FIG. 1 is a flow chart of a method of the present application.

The present application discloses a method for improving an identification accuracy of mixture components by using a known mixture Raman spectrum. Referring to the flow chart shown in FIG. 1, the method includes the following steps:

Step S1: A Raman spectrum standard library and a known mixture library are established. The Raman spectrum standard library includes pure substance Raman spectrum characteristic vector groups of N kinds of pure substances. The known mixture library includes known mixture Raman spectrum characteristic vector groups of M kinds of known mixtures. Each kind of the known mixtures is formed by mixing K kinds of pure substances. The K kinds of pure substances may be either included in the Raman spectrum standard library or not included in the Raman spectrum standard library. N, M and K are integers. Values of N and M are generally large. K is at least greater than or equal to 2.

The N kinds of pure substances are obtained. A method for acquiring a pure substance Raman spectrum characteristic vector group of any nth kind of pure substance therein is as follows, where n is a parameter and $1 \leq n \leq N$:

1. Raman spectrum data of this kind of pure substance is acquired. Specifically, the spectrum data of this kind of pure substance is collected, and data within a Raman shift range of 240 cm$^{-1}$ to 2400 cm$^{-1}$ is selected as original spectrum data of this kind of pure substance. The actually obtained original spectrum data contains noise and a continuous baseline due to the influence caused by the characteristics of the mixture itself, the performance of instruments, environmental information, etc., which will greatly affect subsequent operations, so that the present application uses continuous wavelet transformation to remove the baseline, uses Mexico-hat wavelet as a wavelet basis function, and uses the penalized least square method to perform denoising processing. The original spectrum data after such processing retains spectral peak information and meanwhile is free of the interference of the noise and the baseline. Finally, interpolation and maximum normalization operations are performed to obtain the Raman spectrum data.

2. The acquired Raman spectrum data is subjected to characteristic extraction. Theoretically, the spectral peak of the Raman spectrum data may be described with a Lorentzian curve. However, due to the influence of various factors such as the accuracy of the instrument and the characteristics of the mixture itself, the spectral peaks of the Raman spectrum data obtained by actual measurements are generally of a Voigt curve. This function is a convolution of Lorentzian curve and Gaussian curve. The mathematical expression of the Voigt function is as follows:

$$I(\lambda) = I_c \left\{ \theta \frac{\omega^2}{(\lambda - \lambda_c)^2 + \omega^2} + (1-\theta)\exp\left[\frac{(\lambda - \lambda_c)^2}{2\omega^2}\right] \right\}$$

where $I(\lambda)$ denotes a Raman intensity at a Raman shift of $\lambda$; $\lambda_c$ denotes a Raman shift at the spectral peak; $I_c$ denotes a Raman intensity at the spectral peak; $\omega$ denotes a full width at half maximum of the spectral peak; and $\theta$ denotes a Gauss-Lorentz coefficient of the spectral peak, and the value range of the coefficient is (0, 1).

The above Voigt function can be used to directly fit the spectral peaks of a single peak interval, i.e., single spectral peaks. Overlapping peaks inevitably exist in the Raman spectrum data to make it extremely difficult to extract characteristic parameters of the overlapping peaks, so that it is necessary to decompose and then fit the overlapping peaks in addition to fitting the single spectral peaks to acquire parameters more conveniently. A slope comparison method may be used to determine overlapping peaks of the spectral peaks of the Raman spectrum data to obtain intervals of the single peaks and the overlapping peaks. The above Voigt function is directly used to fit the single peak interval. The spectral peaks of the overlapping peak interval may be regarded as a linear superposition of l Voigt functions, and the mathematical expression thereof is:

$$I(\lambda) = \sum_{t=1}^{l} I_t \left\{ \theta_t \frac{\omega_t^2}{(\lambda - \lambda_t)^2 + \omega_t^2} + (1-\theta_t)\exp\left[-\frac{(\lambda - \lambda_t)^2}{2\omega_t^2}\right] \right\};$$

t is an intermediate parameter, and the meanings of respective rest variables are the same as the meanings of the corresponding variables in the above single peaks.

Based on the above two formulas, a curve fitting method based on a Levenberg-Marquardt algorithm is used to perform spectral peak fitting to obtain characteristic vectors of each spectral peak, including the Raman shift, the Raman intensity, the full width at half maximum and the Gauss-Lorentz coefficient of the spectral peak. Since the Gauss-Lorentz coefficient is random, the present application uses the Raman shift, the Raman intensity, and the full width at half maximum as the characteristic parameters of one spectral peak. The characteristic vectors of respective spectral peaks constitute a Raman spectrum characteristic vector group according to an order of the Raman shifts from small to large.

Therefore, it can be obtained that the pure substance Raman spectrum characteristic vector group of the nth kind of pure substance is expressed as:

$$[\lambda_1{}'', I_1{}'', \omega_1{}''; \lambda_2{}'', I_2{}'', \omega_2{}''; \ldots ; \lambda_i{}'', I_i{}'', \omega_i{}''; \ldots ]$$

where $\lambda$ denotes the Raman shift of the spectral peak; I denotes the Raman intensity of the spectral peak; $\omega$ denotes the full width at half maximum of the spectral peak; $[\lambda_i{}'', I_i{}'', \omega_i{}'']$ denotes the characteristic vector of any ith spectral peak in the pure substance Raman spectrum characteristic vector group of the nth kind of pure substance; and i is a parameter. The Raman spectrum standard library can be obtained by construction after the pure substance Raman spectrum characteristic vector groups of the N kinds of pure substances are obtained by the above method.

Similarly, after the M kinds of known mixtures are acquired, the same processing method above may be used to obtain a mixture Raman spectrum characteristic vector group of each kind of known mixture, so that the known mixture library may be obtained by construction.

For example, in one experimental instance, pure substances of 204 kinds of common chemicals and controlled items are selected to construct the Raman spectrum standard library, and then ethyl alcohol, acetonitrile, acetone, cyclohexane, diacetone alcohol, and diethyl malonate are used to prepare 8 kinds of mixtures, where 5 kinds of ternary mixtures and 3 kinds of quaternary mixtures are prepared. In consideration of the randomness of the concentration ratios of the known mixtures in practical applications, each kind of mixture is prepared in a plurality of concentration ratios in the present invention, where each kind of ternary mixture has 9 concentration ratios, and each kind of quaternary mixture has 12 concentration ratios; then a mixture with one concentration ratio is randomly selected from each kind of mixture as a known mixture; and 8 kinds of known mixtures selected are used to construct the known mixture library.

Step S2: A to-be-tested Raman spectrum characteristic vector group of a to-be-tested mixture is acquired. The method for obtaining the to-be-tested Raman spectrum characteristic vector group is the same as the above method for obtaining the pure substance Raman spectrum characteristic vector group, which is not detailed in the present application. The obtained to-be-tested Raman spectrum characteristic vector group may be expressed as:

$$[\lambda_1^T, I_1^T, \omega_1^T; \lambda_2^T, I_2^T, \omega_2^T; \ldots; \lambda_k^T, I_k^T, \omega_k^T; \ldots]$$

where $[\lambda_k^T, I_k^T, \omega_k^T]$ denotes the characteristic vector of any kth spectral peak in the to-be-tested Raman spectrum characteristic vector group, and k is a parameter.

Step S3: A first similarity between the to-be-tested Raman spectrum characteristic vector group and the pure substance Raman spectrum characteristic vector group of the nth kind of pure substance in the Raman spectrum standard library is calculated, where n is a parameter, and a starting value of n is 1. The method for calculating the first similarity specifically includes the following sub-steps:

Step S3a: For any jth spectral peak in the pure substance Raman spectrum characteristic vector group of the nth kind of pure substance, the kth spectral peak that is closest to the jth spectral peak in the to-be-tested Raman spectrum characteristic vector group is determined, where the characteristic vector of the jth spectral peak is expressed as $[\lambda_j^n, I_j^n, \omega_j^n]$, and the characteristic vector of the kth spectral peak is expressed as $[\lambda_k^T, I_k^T, \omega_k^T]$.

Step S3b: An absolute value $51 \lambda_j^n - \lambda_k^T|$ of a difference value of Raman shifts and an absolute value $|\omega_j^n - \omega_k^T|$ of a difference value of full widths at half maximum between the jth spectral peak and the kth spectral peak are calculated, and a fuzzy membership function is used to perform a calculation based on the absolute value of the difference value between the Raman shifts to obtain a Raman shift similarity and to perform a calculation based on the absolute value of the difference value between the full widths at half maximum to obtain a full width at half maximum similarity. The calculation formula is:

$$S_j(x) = \begin{cases} 1 & x \leq l_1 \\ \exp\left(\frac{-(x-l_1)^2}{2c^2}\right) & l_1 < x < l_2 \\ 0 & x \geq l_2 \end{cases}$$

where when the fuzzy membership function is used to calculate the Raman shift similarity, x is the absolute value of the difference value between the Raman shifts, and corresponding $S_j(x)$ is the Raman shift similarity, $l_1=5$, $l_2=15$, and $c=5$. When the fuzzy membership function is used to calculate the full width at half maximum similarity, x is the absolute value of the difference value between the full widths at half maximum, and corresponding $S_j(x)$ is the full width at half maximum similarity, $l_1=3$, $l_2=20$, and $c=3$.

Step S3c: The similarity $$S_j = \frac{S_j(\lambda) + S_j(\omega)}{2}$$

between the jth spectral peak and the kth spectral peak is obtained by calculation based on the Raman shift similarity and the full width at half maximum similarity, where $S_j(\lambda)$ is the Raman shift similarity, and $S_j(\omega)$ is the full width at half maximum similarity.

Step S3d: Similarities between all spectral peaks in the pure substance Raman spectrum characteristic vector group of the nth kind of pure substance and the closest spectral peaks in the to-be-tested Raman spectrum characteristic vector group are calculated, and the first similarity is obtained by calculation according to the following formula:

$$S^n = \sum_j \left(\frac{I_j^n}{\Sigma I^n} \times S_j\right)$$

where $S^n$ denotes the first similarity between the to-be-tested Raman spectrum characteristic vector group and the pure substance Raman spectrum characteristic vector group of the nth kind of pure substance; $I_j^n$ denotes the Raman intensity of the jth spectral peak in the pure substance Raman spectrum characteristic vector group of the nth kind of pure substance; and $\Sigma I^n$ denotes the sum of the Raman intensities of all spectral peaks in the pure substance Raman spectrum characteristic vector group of the nth kind of pure substance. A weight factor $$\frac{I_j^n}{\Sigma I^n}$$

is introduced in the above formula. A relatively large weight is endowed to spectral peaks with relatively high intensity, otherwise the weight is reduced, so that the influence of potential false spectral peaks with relatively low intensity on the calculation of the similarities is reduced.

Step S4: Whether a reference known mixture exists in the known mixture library is detected. The reference known mixture is a known mixture containing the nth kind of pure substance from among the M kinds of known mixtures of the known mixture library, that is, the nth kind of pure substance is a component of the reference known mixture.

Step S5: If no reference known mixture exists in the known mixture library, the similarity between the to-be-tested mixture and the nth kind of pure substance is determined to be the first similarity obtained by calculation in step S3.

Step S6: If Q kinds of reference known mixtures exist in the known mixture library, the reference known mixtures are used to assist in searching to further reduce the influence of the offset of the spectral peaks on the calculation of the similarity. Specifically, for any qth kind of reference known mixture:

Step S6a: A spectral peak characteristic vector group with offset information corresponding to the nth kind of pure substance in the known mixture Raman spectrum characteristic vector group of the qth kind of reference known mixture is extracted. Specifically:

(1) for any ith spectral peak in the pure substance Raman spectrum characteristic vector group of the nth kind of pure substance, an sth spectral peak that is closest to the ith spectral peak from among the known mixture Raman spectrum characteristic vector group of the qth kind of reference known mixture is determined, where the characteristic vector of the ith spectral peak is expressed as $[\lambda_i^n, I_i^n, \omega_i^n]$, and the characteristic vector of the sth spectral peak is expressed as $[\lambda_s^q, I_s^q, \omega_s^q]$;

(2) if the sth spectral peak satisfies $d \leq h_1$ or the sth spectral peak satisfies $h_1 < d < h_2, S_i(\omega) \geq S_\omega$, the sth spectral peak is determined to be an offset spectral peak corresponding to the ith spectral peak, where $d = |\lambda_i^n - \lambda_s^q|$ denotes an absolute value of a difference value of Raman shifts between the two spectral peaks; $\omega = |\omega_i^n - \omega_s^q|$ denotes an absolute value of a difference value of full widths at half maximum between the two spectral peaks; $S_i(\omega)$ is a full width at half maximum similarity calculated using the fuzzy membership function based on the absolute value of a difference value of the full widths at half maximum; a calculation formula refers to step S3b above; $h_1, h_2$ and $S_w$ are all preset thresholds, and $h_1 = 5$, $h_2 = 15$, and $S_w = 0.6$ are set in the present application; that is, the calculation formula can be expressed as:

$$[\lambda_i^{mdb}, I_i^{mdb}, \omega_i^{mdb}] = \begin{cases} [\lambda_s^q, I_s^q, \omega_s^q] & d \leq h_1 \\ [\lambda_s^q, I_s^q, \omega_s^q] & h_1 < d < h_2, S_i(\omega) \geq S_\omega \\ \times & \text{others} \end{cases}$$

$[\lambda_i^{mdb}, I_i^{mdb} \omega_i^{mdb}]$ is the characteristic vector of the offset spectral peak corresponding to the ith spectral peak; and (3) the offset spectral peaks corresponding to all spectral peaks in the pure substance Raman spectrum characteristic vector group of the nth kind of pure substance are obtained by calculation, so that the spectral peak characteristic vector group with the offset information of the nth kind of pure substance is obtained, which may be expressed as $[\lambda_1^{mdb}, I_1^{mdb}, \omega_1^{mdb}; \ldots \lambda_i^{mdb}, I_i^{mdb}, \omega_i^{mdb}; \ldots]$.

Step S6b: A second similarity between the spectral peak characteristic vector group with the offset information and the to-be-tested Raman spectrum characteristic vector group is calculated. The specific calculation method is the same as the above method for calculating the first similarity, which is not detailed in the present application.

The above q is a parameter started from 1, and the above steps are cyclically executed to obtain Q second similarities by calculation. To determine that the similarity between the to-be-tested mixture and the nth kind of pure substance is the maximum value from the first similarity and the Q second similarities, the actual practice is usually that: the first similarity $S^n$ obtained by calculation in step S3 above is endowed to an initial similarity; for the first kind of reference known mixture, the above method is used to calculate to obtain the corresponding second similarity; and if the second similarity is greater than the initial similarity, i.e., the first similarity, the second similarity is endowed to the initial similarity, that is, the initial similarity is updated to the second similarity obtained by the current calculation, otherwise the initial similarity is kept as the first similarity. For the second kind of reference known mixture, the above method continues to be used to calculate to obtain a corresponding second similarity, which is compared with the initial similarity at this time, and the initial similarity at this time is updated or maintained according to a comparison result till the initial similarity obtained in case of q=Q is the maximum value from the first similarity and the Q second similarities, i.e., the similarity between the to-be-tested mixture and the nth kind of pure substance is determined to be obtained.

Step S7: After it is determined that the similarity between the to-be-tested mixture and the nth kind of pure substance is obtained, n=n+1 is set, and the above steps S3 to S6 are re-executed till N similarities between the to-be-tested mixture and the N kinds of pure substances are obtained in case of n=N.

Step S8: P kinds of pure substances with the highest similarity are selected as a component identification result of the to-be-tested mixture, and P is a parameter with a predetermined value such as P=7.

Figure 2:
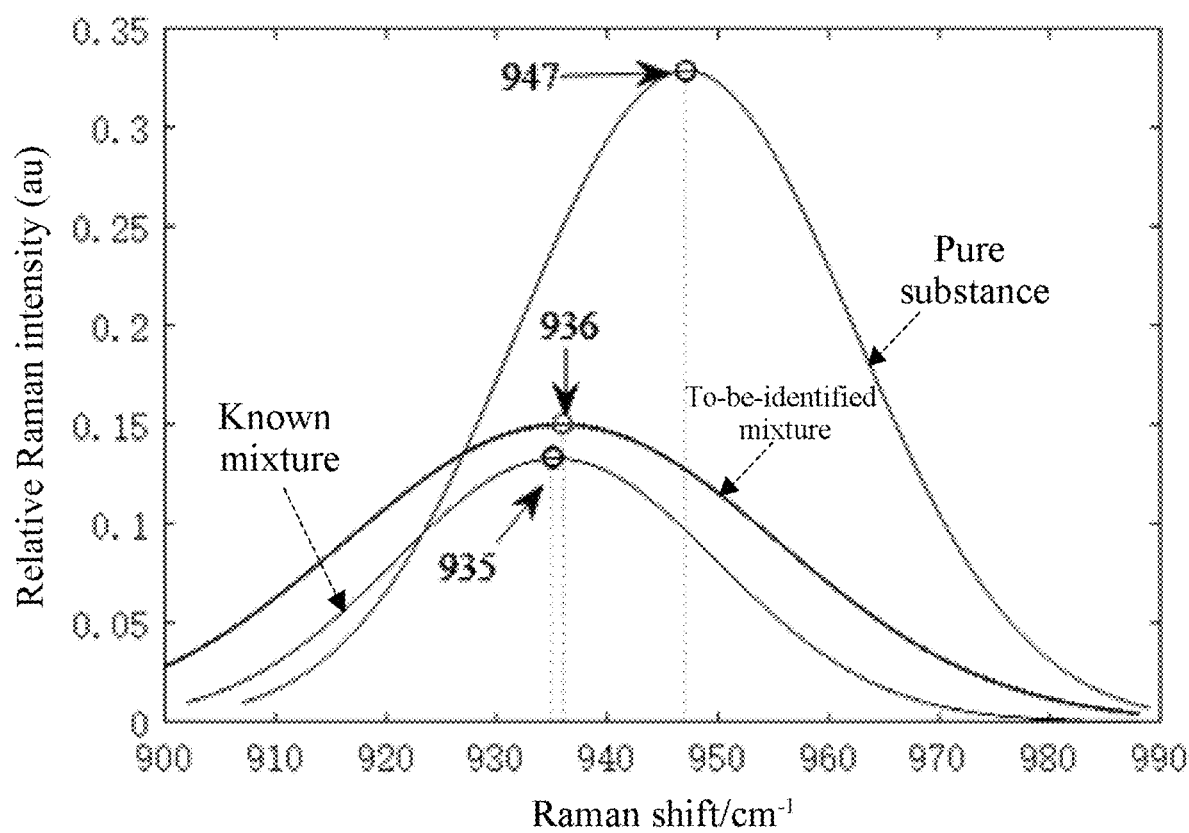
FIG. 2 is a schematic diagram of the offset of a Raman shift of spectral peaks of a known mixture and a to-be-identified mixture relative to a pure substance.

The present application uses the known mixture library to assist the Raman spectrum standard library in searching. In the schematic experimental diagram shown in FIG. 2, the Raman shift of the spectral peak of the pure substance is 947 cm$^{-1}$, and the Raman shifts of the known mixture and the to-be-identified mixture are respectively offset to 935 cm$^{-1}$ and 936 cm$^{-1}$. Due to the existence of the offset phenomenon, if only a pure substance library search strategy is used at this time, a great error will be brought to the calculation of the spectral peak similarity, but the application of the known mixtures in the present application effectively compensates for the interferences caused by the offset phenomenon. Therefore, compared to establishing a pure substance library only, the use of the known mixtures can effectively assist in improving the identification accuracy of a to-be-identified substance.

The above descriptions are merely preferred implementations of the present application, and the present invention is not limited to the above embodiments. It can be understood that other improvements and changes directly derived or associated by those skilled in the art, without departing from the spirit and conception of the present invention, shall all fall within the protection scope of the present invention.

What is claimed is:

1. A method for improving an identification accuracy of mixture components by using a known mixture Raman spectrum, the method comprising:
   establishing a Raman spectrum standard library and a known mixture library, wherein the Raman spectrum standard library comprises pure substance Raman spectrum characteristic vector groups of N kinds of pure substances; the known mixture library comprises known mixture Raman spectrum characteristic vector groups of M kinds of known mixtures; and each kind of the known mixtures is formed by mixing K kinds of pure substances;
   acquiring a to-be-tested Raman spectrum characteristic vector group of a to-be-tested mixture;
   calculating a first similarity between the to-be-tested Raman spectrum characteristic vector group and a pure substance Raman spectrum characteristic vector group of an nth kind of pure substance in the Raman spectrum standard library, and detecting whether a reference known mixture exists in the known mixture library, wherein the reference known mixture is a known mixture containing the nth kind of pure substance from among the M kinds of known mixtures; n is a parameter, and a starting value of n is 1;

if no reference known mixture exists in the known mixture library, determining that a similarity between the to-be-tested mixture and the nth kind of pure substance is the first similarity;

if Q kinds of reference known mixtures exist in the known mixture library, extracting a spectral peak characteristic vector group with offset information corresponding to the nth kind of pure substance in the known mixture Raman spectrum characteristic vector group of each kind of reference known mixture, and calculating a second similarity between the spectral peak characteristic vector group with the offset information and the to-be-tested Raman spectrum characteristic vector group; and determining that the similarity between the to-be-tested mixture and the nth kind of pure substance is a maximum value from the first similarity and Q second similarities;

after determining that the similarity between the to-be-tested mixture and the nth kind of pure substance is obtained, setting n=n+1, and re-executing steps of calculating the first similarity between the to-be-tested Raman spectrum characteristic vector group and the pure substance Raman spectrum characteristic vector group of the nth kind of pure substance in the Raman spectrum standard library and detecting whether a reference known mixture exists in the known mixture library, till N similarities between the to-be-tested mixture and the N kinds of pure substances are obtained in case of n=N; and selecting P kinds of pure substances with the highest similarity as a component identification result of the to-be-tested mixture.

2. The method according to claim 1, wherein the extracting a spectral peak characteristic vector group with offset information corresponding to the nth kind of pure substance in the known mixture Raman spectrum characteristic vector group of each kind of reference known mixture comprises, for any qth kind of reference known mixture:

determining an sth spectral peak that is closest to an ith spectral peak from among the known mixture Raman spectrum characteristic vector group of the qth kind of reference known mixture, for any ith spectral peak in the pure substance Raman spectrum characteristic vector groups of the nth kind of pure substance, wherein the characteristic vector of the ith spectral peak is expressed as $[\lambda_i'', I_i'', \omega_i'']$, and the characteristic vector of the sth spectral peak is expressed as $[\lambda_s^q, I_s^q, \omega_s^q]$, wherein $\lambda$ denotes a Raman shift of the spectral peak; I denotes a Raman intensity of the spectral peak; and $\omega$ denotes a full width at half maximum of the spectral peak;

if the sth spectral peak satisfies $d \leq h_1$ or the sth spectral peak satisfies $h_1 < d < h_2, S_i(\omega) \geq S_\omega$, determining that the sth spectral peak is an offset spectral peak corresponding to the ith spectral peak, wherein $d = |\lambda_i'' - \lambda_s^q|$ denotes an absolute value of a difference value of Raman shifts between two spectral peaks; $\omega = |\omega_i'' - \omega_s^q|$ denotes an absolute value of a difference value of full widths at half maximum between two spectral peaks; $S_i(\omega)$ is a full width at half maximum similarity calculated using a fuzzy membership function based on the absolute value of the difference value of the full widths at half maximum; and $h_1$, $h_2$, and $S_\omega$ are all preset thresholds; and calculating to obtain the offset spectral peaks corresponding to all spectral peaks in the pure substance Raman spectrum characteristic vector group of the nth kind of pure substance, and to obtain the spectral peak characteristic vector group with offset information of the nth kind of pure substance.

3. The method according to claim 1, wherein the calculating the first similarity between the to-be-tested Raman spectrum characteristic vector group and the pure substance Raman spectrum characteristic vector group of the nth kind of pure substance in the Raman spectrum standard library comprises:

determining a kth spectral peak that is closest to a jth spectral peak in the to-be-tested Raman spectrum characteristic vector group for any jth spectral peak in the pure substance Raman spectrum characteristic vector group of the nth kind of pure substance, wherein the characteristic vector of the jth spectral peak is expressed as $[\lambda_j'', I_j'', \omega_j'']$, and the characteristic vector of the kth spectral peak is expressed as $[\lambda_k^T, I_k^T, \omega_k^T]$, wherein $\lambda$ denotes a Raman shift of the spectral peak; I denotes a Raman intensity of the spectral peak; and $\omega$ denotes a full width at half maximum of the spectral peak;

calculating an absolute value of a difference value of Raman shifts and an absolute value of a difference value of full widths at half maximum between the jth spectral peak and the kth spectral peak, and using a fuzzy membership function to perform a calculation based on the absolute value of the difference value between the Raman shifts to obtain a Raman shift similarity and to perform a calculation based on the absolute value of the difference value between the full widths at half maximum to obtain a full width at half maximum similarity;

calculating, based on the Raman shift similarity and the full width at half maximum similarity, to obtain the similarity $$S_j = \frac{S_j(\lambda) + S_j(\omega)}{2}$$

between the jth spectral peak and the kth spectral peak, wherein $S_j(\lambda)$ is the Raman shift similarity, and $S_j(\omega)$ is the full width at half maximum similarity;

calculating to obtain similarities between all spectral peaks in the pure substance Raman spectrum characteristic vector group of the nth kind of pure substance and the closest spectral peaks in the to-be-tested Raman spectrum characteristic vector group, and obtaining the first similarity by calculation according to the following formula:

$$S^n = \sum_j \left( \frac{I_j^n}{\Sigma I^n} \times S_j \right)$$

wherein $S^n$ denotes the first similarity between the to-be-tested Raman spectrum characteristic vector group and the pure substance Raman spectrum characteristic vector group of the nth kind of pure substance; $I_j^n$ denotes a Raman intensity of the jth spectral peak in the pure substance Raman spectrum characteristic vector group of the nth kind of pure substance; and $\Sigma I^n$ denotes a sum of Raman intensities of all spectral peaks in the pure substance Raman spectrum characteristic vector group of the nth kind of pure substance.

4. The method according to claim 2, wherein a calculation method of the fuzzy membership function is:

$$S_j(x) = \begin{cases} 1 & x \leq l_1 \\ \exp\left(\dfrac{-(x-l_1)^2}{2c^2}\right) & l_1 < x < l_2 \\ 0 & x \geq l_2 \end{cases}$$

wherein when the fuzzy membership function is used to calculate the Raman shift similarity, x is the absolute value of the difference value between the Raman shifts, and corresponding $S_j(x)$ is the Raman shift similarity, $l_1=5$, $l_2=15$, and $c=5$; and when the fuzzy membership function is used to calculate the full width at half maximum similarity, x is the absolute value of the difference value between the full widths at half maximum, and corresponding $S_j(x)$ is the full width at half maximum similarity, $l_1=3$, $l_2=20$, and $c=3$.

5. The method according to claim 1, wherein for any substance in the pure substance, the known mixture and the to-be-tested mixture, a method for acquiring a Raman spectrum characteristic vector group corresponding to the substance comprises:

acquiring Raman spectrum data of the substance;

determining, using a slope comparison method, overlapping peaks of spectral peaks of the Raman spectrum data to obtain intervals of single peaks and overlapping peaks, fitting the spectral peaks using a Voigt function, and expressing the spectral peaks of a single peak interval as follows:

$$I(\lambda) = I_c\left\{\theta\dfrac{\omega^2}{(\lambda-\lambda_c)^2+\omega^2} + (1-\theta)\exp\left[\dfrac{(\lambda-\lambda_c)^2}{2\omega^2}\right]\right\}$$

expressing the spectral peaks of an overlapping peak interval as a linear superposition of the Voigt function as below:

$$I(\lambda) = \sum_{t=1}^{l} I_t\left\{\theta_t\dfrac{\omega_t^2}{(\lambda-\lambda_t)^2+\omega_t^2} + (1-\theta_t)\exp\left[-\dfrac{(\lambda-\lambda_t)^2}{2\omega_t^2}\right]\right\}$$

wherein $I(\lambda)$ denotes a Raman intensity at a Raman shift of $\lambda$; $\lambda_c$ denotes a Raman shift at the spectral peak; $I_c$ denotes a Raman intensity at the spectral peak; $\omega$ denotes a full width at half maximum of the spectral peak; and $\theta$ denotes a Gauss-Lorentz coefficient of the spectral peak; l is a number of the overlapping peaks in the overlapping peak interval;

fitting the spectral peaks using a curve fitting method based on a Levenberg-Marquardt algorithm to obtain characteristic vectors of each spectral peak, comprising the Raman shift, the Raman intensity, and the full width at half maximum of the spectral peak; and constituting a Raman spectrum characteristic vector group using the characteristic vectors of each spectral peak according to an order of the Raman shifts from small to large.

6. The method according to claim 5, wherein the acquiring the Raman spectrum data of the substance comprises:

collecting original spectrum data within a Raman shift range of 240 $cm^{-1}$ to 2400 $cm^{-1}$ of the substance;

removing baselines from the original spectrum data using continuous wavelet transformation with Mexico-hat wavelet as a wavelet basis function, and performing denoising processing using a penalized least square method; and performing interpolation and maximum normalization operations on the original spectrum data after baseline removal and denoising processing to obtain the Raman spectrum data.

* * * * *